(12) United States Patent
Alligood (10) Patent No.: US 10,478,351 B2
(45) Date of Patent: Nov. 19, 2019

(54) ABSORBENT INCONTINENCE ARTICLE AND METHOD WITH ADJUSTABLE ENGAGING PLACEMENT

(71) Applicant: Lawrence M. Alligood, Carrollton, GA (US)

(72) Inventor: Lawrence M. Alligood, Carrollton, GA (US)

(\*) Notice: Subject to any disclaimer, the term of this patent is extended or adjusted under 35 U.S.C. 154(b) by 491 days.

(21) Appl. No.: 15/183,791

(22) Filed: Jun. 16, 2016

(65) Prior Publication Data

US 2016/0367410 A1    Dec. 22, 2016

Related U.S. Application Data (60) Provisional application No. 62/181,184, filed on Jun. 17, 2015.

(51) Int. Cl.
*A61F 13/15* (2006.01)
*A61F 13/471* (2006.01)
(Continued)

(52) U.S. Cl.
CPC ........ *A61F 13/471* (2013.01); *A61F 13/4704* (2013.01); *A61F 13/474* (2013.01);
(Continued)

(58) Field of Classification Search
CPC ............. A61F 13/471; A61F 13/4704; A61F 13/47236; A61F 13/474; A61F 13/5616; A61F 2013/5694; A61F 2013/8497
(Continued)

(56) References Cited

U.S. PATENT DOCUMENTS 4,576,599 A    3/1986  Lipner
4,964,860 A *  10/1990  Gipson ............... A61F 5/4401
                                                            604/391
(Continued)

FOREIGN PATENT DOCUMENTS

CA    2190723 A1    11/1995
CA    2547548 C     6/2009

OTHER PUBLICATIONS

International Searching Authority, Israel Patent Office, PCT Notification of transmittal of the International Search Report and the Written Opinion of the International Searching Authority, or the Declaration (Application No. PCT/US2016/038247), dated Oct. 13, 2016, 8 pages, Israel/U.S.

*Primary Examiner* — Jacqueline F Stephens
(74) *Attorney, Agent, or Firm* — M. William Blackburn (57) ABSTRACT

Embodiments of the disclosure provide for improved adjustability and engaging placement of absorbent incontinence articles. An absorbent article designed to fit various body contours and sizes and facilitate placements of the scrotum or genitals for comfort. An absorbent article may include a structure materials to absorb fluid, for instance a paper or napkin-like article made using virgin fiber or recycled fibers in order to achieve certain softness and strength attributes. The article, for instance a sheath, liner, or barrier, is adapted to provide at least one split or cleft, and thus absorbent flaps, at the bottom of the barrier to engage a crotch of the underwear and restrict movement of the article and facilitate comfortable placement of genitals as preferred and to achieve an engaged geometry of article with underwear. The absorbent article also includes graduated placement indicia to facilitate retention of proper fit based on body size.

7 Claims, 7 Drawing Sheets

(51) Int. Cl.
   *A61F 13/47*     (2006.01)
   *A61F 13/474*    (2006.01)
   *A61F 13/56*     (2006.01)
   *A61F 13/472*    (2006.01)
   *A61F 13/84*     (2006.01)

(52) U.S. Cl.
   CPC .... *A61F 13/47236* (2013.01); *A61F 13/5616* (2013.01); *A61F 13/5694* (2013.01); *A61F 2013/8497* (2013.01)

(58) Field of Classification Search
   USPC ......... 604/349, 347, 385.14, 385.16, 385.19, 604/385.201
   See application file for complete search history.

(56) References Cited

U.S. PATENT DOCUMENTS

| | | | |
|---|---|---|---|
| 5,342,332 A | | 8/1994 | Wheeler |
| 5,383,867 A | * | 1/1995 | Klinger ................ A61F 5/4401 604/358 |
| 5,558,734 A | | 9/1996 | Sherrod et al. |
| 5,651,778 A | | 7/1997 | Melius et al. |
| 5,690,627 A | * | 11/1997 | Clear ................ A61F 13/15593 604/385.29 |
| 5,702,381 A | | 12/1997 | Cottenden |
| 5,843,065 A | † | 12/1998 | Wyant |
| 6,296,929 B1 | | 10/2001 | Gentile et al. |
| 6,371,950 B1 | | 4/2002 | Rolansky et al. |
| 6,475,197 B1 | | 11/2002 | Krzysik et al. |
| 6,479,726 B1 | | 11/2002 | Cole |
| 6,565,548 B1 | | 5/2003 | Glaug et al. |
| 6,569,135 B1 | | 5/2003 | Muia |
| 8,425,481 B2 | | 4/2013 | Lindstrom |
| 8,889,946 B2 | | 11/2014 | Hermansson et al. |
| 8,986,271 B1 | * | 3/2015 | Horne ................ A61F 5/4408 604/349 |
| 2005/0261658 A1 | † | 11/2005 | Baumchen |
| 2006/0047260 A1 | * | 3/2006 | Ashton ................ A61F 13/496 604/396 |
| 2008/0119816 A1 | † | 5/2008 | Carstens |
| 2010/0280477 A1 | * | 11/2010 | Henderson ........ A61F 13/49004 604/385.15 |
| 2013/0090618 A1 | | 4/2013 | Alshammari |
| 2016/0008188 A1 | † | 1/2016 | Lumaque-Steeman |

\* cited by examiner
† cited by third party

ABSORBENT INCONTINENCE ARTICLE AND METHOD WITH ADJUSTABLE ENGAGING PLACEMENT

CROSS REFERENCE AND PRIORITY TO A RELATED APPLICATION

Under provisions of 35 U.S.C. 119, this non-provisional patent application claims priority to and the benefit of U.S. Provisional Application No. 62/181,184, filed on 17 Jun. 2015, by Lawrence M. Alligood, entitled "Absorbent Incontinence Article and Method with Adjustable Conforming Fit", which is incorporated herein by reference in its entirety.

COPYRIGHT

All rights, including copyrights, in the material included herein are vested in and are the property of the Applicant. The Applicant retains and reserves all rights in the material included herein, and grants permission to reproduce the material only in connection with reproduction of the granted patent and for no other purpose.

FIELD

The field of this invention relates generally to disposable absorbent fiber articles for absorbing fluids resulting from male urinary incontinence and more particularly to disposable absorbent shields, barriers, liners, sheaths, layers, or napkins having an adjustable, conforming, and engaging placement and method.

BACKGROUND

Urinary incontinence, especially in some adult men, can be embarrassing and problematic. This problem is particularly acute for male adults who experience urinary flow irregularities, such as slow and intermittent urine dribbling and unpredictable dribbling. Often, the residual urine can flow unchecked which can soil, splotch, or stain the underclothing or trousers and cause embarrassment and discomfort. This condition can cause the affected individual emotional distress and adversely impact his personal esteem, mobility, and quality of life. Further, this residual moisture may irritate the skin of the scrotum and perineum. Conventional methods for addressing this problem include pads or diapers that often are uncomfortable or don't appeal to men. For example, men may feel embarrassed or are emotionally distressed by wearing a product that is similar to a diaper or a female menstrual cycle pad.

Moreover, conventional products are complex and may not adequately fit some of the men or include sufficient instructions for proper placement. Further, the necessity of making a variety of sizes available cause's consumers of conventional products to guess at what size is suitable for their particular body build and size. And, businesses must carry inventory of multiple product sizes, which often increases business costs. Although various devices and absorbent products have been proposed in the past to cope with these problems, these products have been too expensive, complex, or impractical in terms of male appeal, comfort, and ease of use. Accordingly, there is a need to provide a male urinary incontinence article and method that overcomes these and other difficulties.

SUMMARY

This Summary is provided to introduce a selection of concepts in a simplified form that are further described below in the Detailed Description. This Summary is not intended to be used to limit the claimed subject matter's scope.

As will be described in greater detail below, the various embodiments of the present disclosure provide for improved adjustability, conforming fit, and engaging placement of disposable absorbent urinary incontinence articles. In particular, embodiments of the present disclosure allow the wearers of the absorbent article to more readily go about their daily tasks without the nuisance of an uncomfortable or embarrassing experience with conventional incontinence products. At least one object of embodiments of the present disclosure is to provide men who experience light, moderate, or non-extreme urinary incontinence, a disposable absorbent article that is designed to fit various body contours and sizes and facilitate various placements of the scrotum or genitals for comfort. In one aspect, a disposable absorbent article may include an absorbent structure that absorbs fluid, for instance a paper or napkin-like article made using virgin fiber or recycled fibers in order to achieve certain softness and strength attributes. The disposable absorbent article, for instance a sheath, liner, shield, layer, or barrier, is adapted to provide at least one split, slit, or cleft, and thus at least two absorbent flaps, at the bottom of the sheath to facilitate comfortable placement of the scrotum or genitals as preferred by the wearer or user of the absorbent article and to achieve a snug, engaged, anchored, or form-fitting geometry and optional placement of more absorbent material where needed in the crotch region. The absorbent article is anchored or engaged as at least one split engages with a crotch (the part of a garment that passes between the legs) of the underwear, undergarment, or undershorts, in particular boxer shorts or boxer briefs to engage and minimize shifting or movement of the absorbent article with respect to the underwear. The absorbent flaps extend down over the underwear crotch region or crotch down toward and over the upper thighs of the user or under the thigh coverings of the underwear as a continuing sheath, liner, or barrier.

In another aspect, embodiments of the present disclosure may include placement or graduated indicia marked on the disposable absorbent article to indicate to a user proper placement of the article with respect to his underwear, torso length, and body size.

Still, in another aspect, a disposable absorbent article with an adjustable, body contour conforming fit and engaging placement may include an absorbent structure that is configured to sufficiently absorb fluid before the fluid reaches the users underclothing and outer clothing even, optionally, without inclusion of an impermeable layer in the absorbent structure. The disposable absorbent structure may include at least a one or two-ply (top sheet and back sheet) fiber based barrier, sheath, layer, or liner with a bottom or lower portion of the structure including at least a two or three-ply or more (top, middle, and bottom) fiber (or other absorbent material) based sheets. The third-ply or third layer may increase absorbency of the article as much as 50 percent compared to including a two-ply lower portion.

Both the foregoing general description and the following detailed description provide examples and are explanatory only. Accordingly, the foregoing general description and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present invention disclosure. In the drawings.

Corresponding reference characters indicate corresponding parts, components, or elements throughout the drawings.

DETAILED DESCRIPTION

It is to be understood by one of ordinary skill in the art that the present disclosure is a description of exemplary embodiments, and is not intended as limiting the broader aspects of the present invention. In general, embodiments of present invention are directed to unobtrusive, convenient, and male-appealing absorbent articles incorporating at least two engaging conforming placement portions or absorbent flaps that may anchor or engage the crotch of an undergarment and extend down toward and over the thighs of the user or thigh coverings of the undergarment as a continuing sheath, liner, or barrier. Embodiments of the present invention also incorporate proper placement indicia, methods of manufacture, and methods of use. In accordance with the present disclosure, the absorbent articles may include multiple paper layers made using virgin fiber or recycled fiber sheaths in order to achieve certain softness, absorbency, and strength attributes. In one embodiment, for instance, the multiple layers or sheets may be configured, attached, or connected together using thread, adhesive, or other adhering or connecting means. In this manner, the wearer experiences a comfortable and discrete fit even when the absorbent article has been insulted with a body fluid, such as urine.

Figure 1:
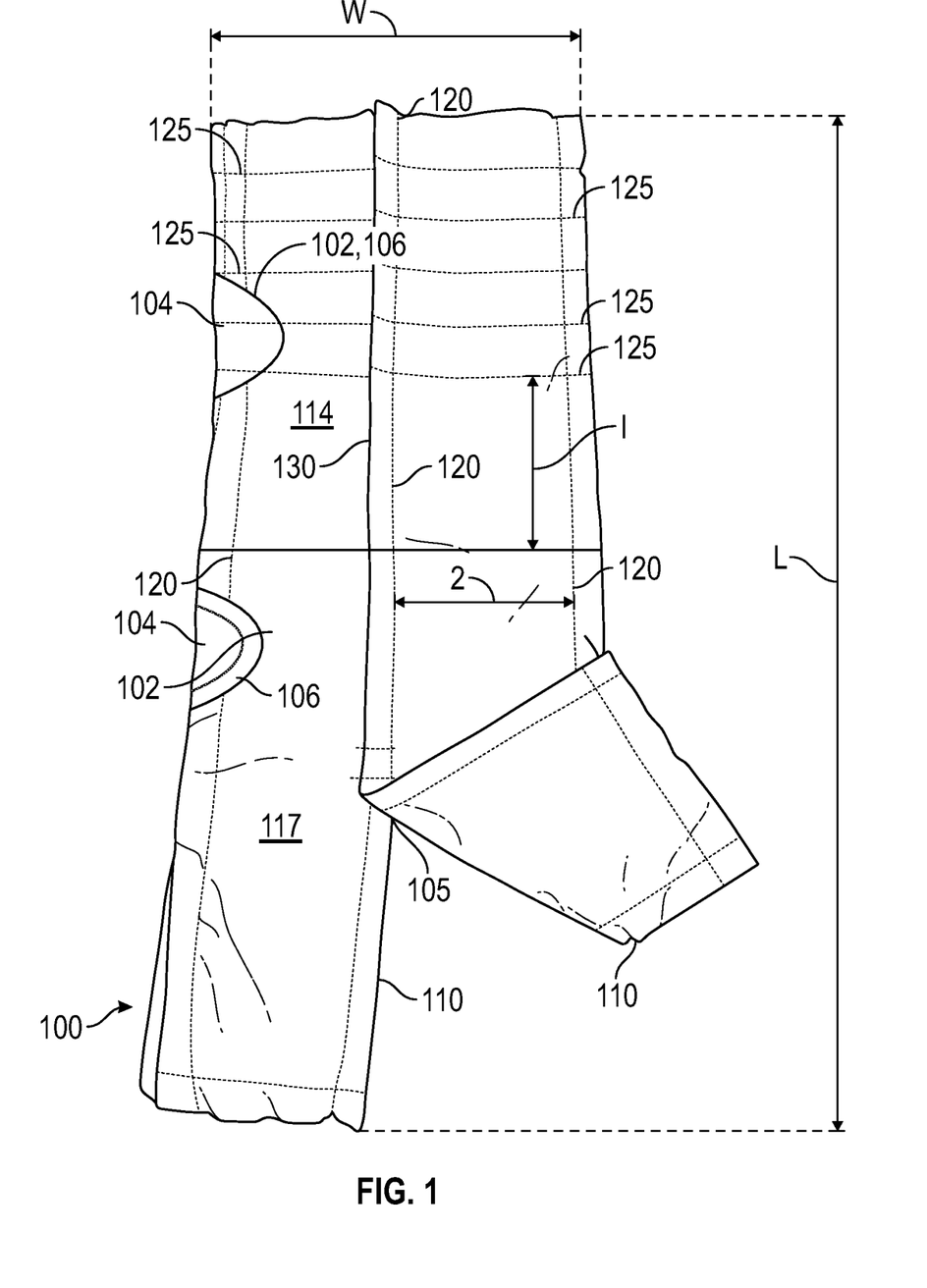
FIG. 1 is a perspective of one suitable embodiment of an absorbent article having an absorbent structure where at least a portion of the structure includes a top sheet, internal sheet and a back, or bottom, sheet.

FIGS. 1-7 illustrate at least three suitable embodiments of a disposable absorbent article, such as an absorbent barrier, sheath, liner, shield, layer, or napkin. FIG. 1 illustrates one absorbent article embodiment indicated generally at 100, configured to absorb fluid, such as bodily fluid. The illustrated disposable absorbent article 100 is sized and shaped to fit a variety of body or torso builds. The length and width of the article may range from about five inches (12.7 cm) to about 12 inches (30.5 cm) or seven (17.8 cm) to nine inches (22.9 cm) in width and from about ten to 24 inches (25.4 to 61 cm) or 18 to 22 inches (45.7 to 55.9 cm) in length.

The absorbent article 100 has a longitudinal direction 1 and a lateral direction 2. An embodiment of the illustrated absorbent article 100, for example, has a length L (i.e., the extent of the absorbent article in the longitudinal direction 1) of approximately 21.5 inches (54.6 cm) and a width W (i.e., the extent of the disposable absorbent article in the lateral direction 2) of approximately 7.5 inches (19 cm). Thus, the illustrated absorbent article 100 is generally rectangular. It is understood that the article 100 can have any suitable length and/or width. It is also understood that the absorbent article 100 can have any suitable shape (e.g., square, circular, elliptical).

As illustrated in FIG. 1, the illustrated absorbent article 100 includes a body-side or top sheet 102, optionally, a garment side back sheet 104, and optionally, within at least a lower portion 117, a middle sheet 106 disposed between the top sheet 102 and the back sheet 104. In the illustrated embodiment, the top sheet 102 and back sheet 104 may extend beyond the periphery of the middle sheet 106 and be sewn or adhesively bonded to each other. It is understood, however, that the top sheet 102 and back sheet 104 can be bonded together about the periphery of the middle sheet 106 using any suitable bonding technique. It is also understood that the top sheet 102, back sheet 104, and middle sheet 106 can be coextensive or that the top sheet and/or back sheet can have an extent less than the middle sheet. It is also understood that across a lower portion 117, the top sheet 102, and the middle sheet 106 or the back sheet 104 and the middle sheet 106 are interchangeable in order. It is also understood that the absorbent article 100 may be solely 1-ply having just the body side top sheet 102 (just 1-ply) in an upper portion 114 having the lower portion 117 with at least a 1 or 2-ply configuration. Alternatively, the lower portion may 117 may solely include at least 1, 2, or 3-ply absorbent material while the upper portion 114 is made of different materials.

More specifically, the male incontinence absorbent article 100 is structured for use with undershorts, underwear, or pants. The absorbent article 100 may include the upper portion 114 and the lower portion 117, where the lower portion 117 includes at least a portion of the absorbent body-side sheet 102 having a split 105 extending longitudinally from an edge of the lower portion 117 toward the upper portion 114 and forming at least two absorbent flaps 110 in the lower portion 117. The split 105 borders at least one side of the absorbent flaps 110. The absorbent flaps 110 are structured to engage with and extend downward beyond a crotch of the undershorts restrict lateral movement, and eventually downward movement, of the absorbent article 100 with respect to the undershorts or underwear. The split 105 may extend a distance greater than zero and less than about half of a length, L, of the absorbent article 100. Optionally, the split 105 may extent a distance greater than about half the length L, but less than L. For example, the split or slit 105 may extend a distance at, or greater than, about a sixteenth of the length L.

Alternatively, as described above, the absorbent article 100 may also include the back sheet 104 within at least the lower portion 117 where the body-side or top sheet 102 is above the back sheet 104. Still further, the article 100 may include the middle sheet 106 between the back sheet 104 and the top sheet 102, the middle sheet 106 being within at least the lower portion 117 of the article 100 where at least the middle sheet 106 and the top sheet 102 are each made from an absorbent material. Thus, the top sheet 102 can be liquid permeable and the back sheet may be liquid impermeable, the top sheet 102 being adjacent to the absorbent middle sheet 106 on a side opposite the back sheet 104. In an alternative embodiment, the back sheet 104 may also be liquid permeable. The back sheet 104 can also be made of an absorbent material and located within the upper portion 114 adjacent to the top sheet 102.

The absorbent article 100 can also include an absorbent wicking fold 130 disposed longitudinally on the top sheet 102 adding absorbent capabilities to the article 100 directing body fluid away from a user's skin. The absorbent article 100 also can include placement indicia 125 disposed on the upper portion 114 to allow a user to retain and adjust placement of the absorbent article 100. A segment of the upper portion 114 placed over a waistband of undershorts or underwear provides a reference point for placement of subsequent absorbent articles as well as restricts movement of the article (downward and upward) with respect to undergarments and garments.

As described in more detail below, the top sheet 102 may be made from a woven fabric, nonwoven fabric, liquid permeable film, or combinations thereof. The middle sheet 106, top sheet 102, and back sheet 104 can be made from cellulose, wood pulp, rayon, cotton, polymeric fibers, and combinations thereof.

With reference now to FIG. 1, the top sheet 102 may include a liquid permeable material, which allows fluids to pass into the top sheet and optionally, into the underling middle sheet 106 and back sheet 104. Absorbent article 100 includes the upper portion 114 and the lower, or bottom portion 117. The upper portion 114 may include at least one or two layers of fiber, napkin, or paper based absorbent material (one or two-ply). The lower portion 117 may include at least one, two, or three layers of fiber, napkin, or paper based absorbent material (one, two, or three-ply) where the absorbency need is greater. Absorbency estimates show that adding the third layer, optionally middle sheet 106, is likely to increase overall absorbency capacity by approximately 50 percent compared to overall capacity without a third layer. The absorbent structure 100 targets an absorbent capacity of the average man with urinary incontinence during an average day. The structure 100 also targets convenience such that a spare absorbent article can be folded and placed in a gentlemen's pocket for future placement on an unusual or extended day.

It should be noted that the body-side top sheet 102 can also include or consist of a layer constructed of any operative material, and may be a composite material. For example, the top sheet 102 may include a woven fabric, a nonwoven fabric, a polymer film, a film-nonwoven fabric laminate or the like, as well as combinations thereof. Examples of a nonwoven fabric useable in the top sheet 102 include, for example, an air-laid nonwoven web, a spunbond nonwoven web, a melt-blown nonwoven web, a bonded-carded web, a hydro-entangled nonwoven web, a spun-lace web or the like, as well as combinations thereof. Other examples of suitable materials for constructing the top sheet 102 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet 102 is a film or a film laminate, the film should be sufficiently apertured or otherwise be made to allow fluids to flow through the top sheet 102 to the absorbent structure 104 or 106.

Other examples of suitable materials for the top sheet 102 are composite materials of a polymer and a nonwoven fabric material. The composite materials are typically in the form of integral sheets generally formed by the extrusion of a polymer to form a nonwoven web, such as a spun-bond material. In a particular arrangement, the top sheet 102 can be configured to be operatively liquid-permeable with regard to the liquids that the pad is intended to absorb or otherwise handle.

It is contemplated that the top sheet 102 can have the same extent as the middle sheet 106 and/or back sheet 104 or can have an extent less or greater than the middle sheet and/or back sheet. It is further contemplated that in some embodiments (not shown), the top sheet 102, middle 106, and/or the bottom sheet 104 can be omitted. Thus, in such embodiments, the disposable absorbent article 100 may comprise the middle sheet 106 and/or the back sheet 104. Other suitable materials which can be used to form the middle sheet 106, top sheet 102, or back sheet 104 include those materials used in absorbent pads, or in 1, 2, or 3-ply napkins or towels, as may be manufactured, for instance by Georgia Pacific Corporation or Kimberly Clark Corporation, and include materials, such as, for example, cellulose, wood pulp fluff, rayon, cotton, and melt-blown polymers such as polyester, polypropylene, various fibers, or coform nonwoven. Coform nonwoven is a melt-blown air-formed combination of melt-blown polymers, such as polypropylene, and absorbent staple fibers, such as cellulose.

The top sheet 102, back sheet 104, and/or the middle sheet 106 can also be formed from a composite comprised of a hydrophilic material which may be formed from various natural or synthetic fibers, wood pulp fibers, regenerated cellulose or cotton fibers, or a blend of pulp and other fibers, One particular example of a material which may be used as the absorbent structure is an air-laid material.

The absorbent article 100 can also include a split, slit, or cleft 105, at least two absorbent flaps 110, connecting means 120, for instance sewn stitching or adhesive connecting the multiple layers or napkins, graduated indicia 125 (optionally perforated), and wicking fold 130. The at least two flaps 110 in the lower portion 117 are configured to fit or engage over the crotch of the user's underwear whether the user comfortably "wears" or places his genitals or scrotum to his left, center, or right. The split 105 facilitates the anchoring or engagement of at least one flap 110 to a crotch of the user's underwear (e.g. boxer shorts or briefs) on the right or left side or center (fold over crotch engagement) for more absorbency and a customized comfort fit that minimizes movement of the absorbent article 100. The flaps 110 extend down toward and over the upper thighs of the user or under thigh coverings of the underwear as a continuing absorbent sheath, liner, or barrier.

Figure 2:
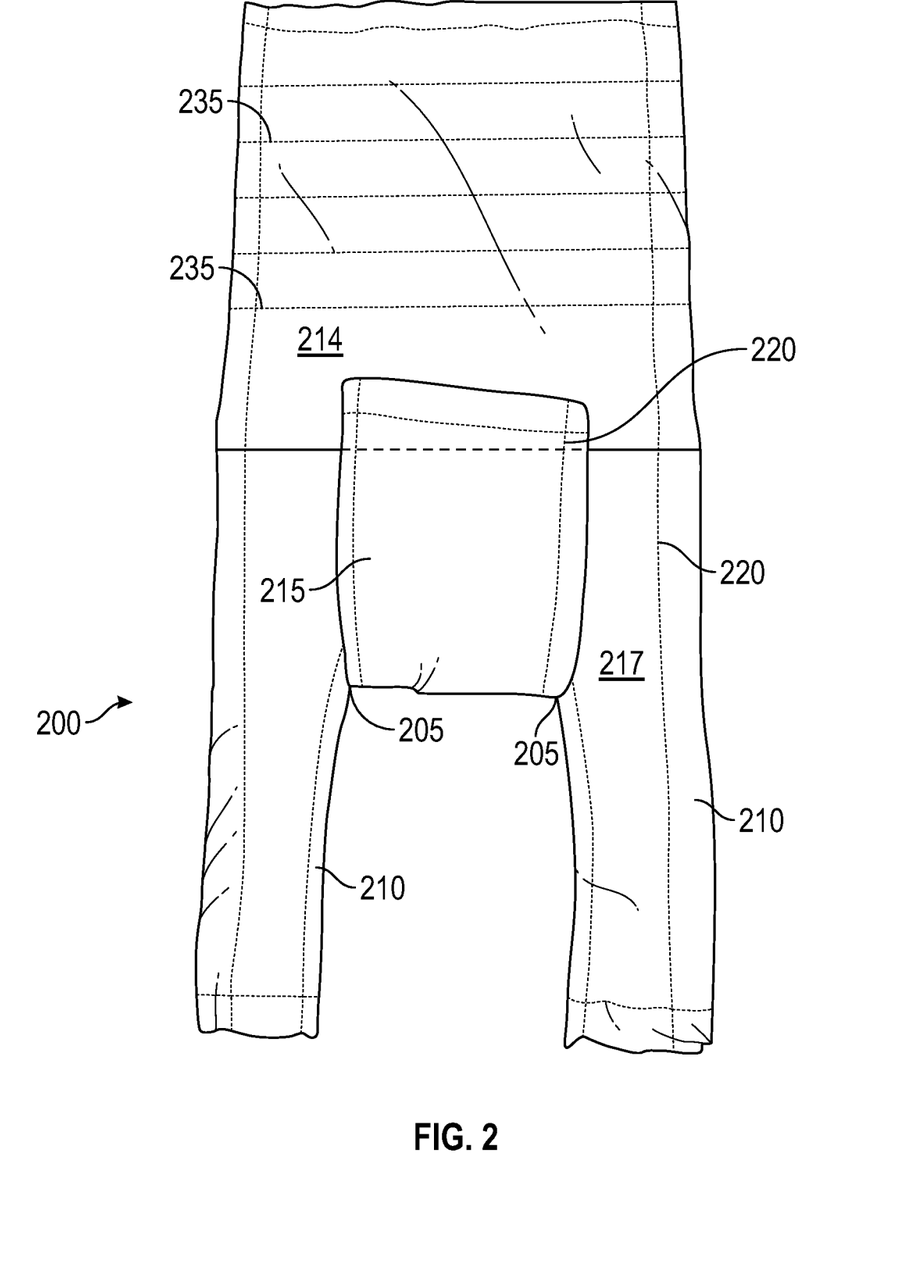
FIG. 2 is a perspective of another suitable embodiment of an absorbent article.

FIG. 2 is a perspective of another suitable embodiment of an absorbent article 200. Absorbent article 200 includes an upper portion 214 and a lower, or bottom, portion 217. The upper portion 214 may include at least one or two layers of fiber, napkin, or paper based absorbent material (one or two-ply). The lower portion 217 may include at least one, two, or three layers of fiber, napkin, or paper based absorbent material (three-ply) where the absorbency need is greater. The absorbent article 200 can also include at least two splits, slits, or clefts 205, at least two small flaps 210, at least one larger flap 215, and connecting means 220, for instance sewn stitching, adhesives, or other bonding elements 220 connecting the multiple layers or napkins. Alternatively, the flaps 210 and 215 may be the same size. The at least two small flaps 210 and the at least one larger flap 215 in the lower portion 217 are configured, structured to fit or engage over the underwear crotch whether the user comfortably "wears" or places his genitals or scrotum to his left, center, or right. The splits 205 facilitate engagement over the underwear crotch 520 (described below with respect to FIG. 5) of at least one flap 210 or 215 on the right or left side or folded over center for more absorbency and a customized comfort placement that minimizes movement of the absorbent article 200 with respect to the user's body and the undergarment. The larger flap 215 allows for flexible placement of even a higher concentration of absorbent capacity within the crotch region as desired by the user.

Similarly, the absorbent article 200 can include the upper portion 214, the lower portion 217, optionally with respect to FIG. 1 the top sheet 102, the back sheet 104, and/or the middle sheet 106 within at least the lower portion 217 of the article 200 between the top 102 and bottom sheets 104, and at least two slits 205 extending longitudinally from an edge of the lower portion 217 toward the upper portion 214 a distance of about less than a half a length of the absorbent article and greater than zero. The two slits 205 define the center flap 215 and the two side flaps 210. The slits or splits 205 may extend toward the upper portion 214 at least a sixteenth of the length of the article 200. The absorbent article 200 may further include placement indicia 235 laterally disposed on the upper portion 214 to allow a user to adjust to and retain a placement setting 235 of the article 200 and subsequent articles of the same size and design.

Figure 3:
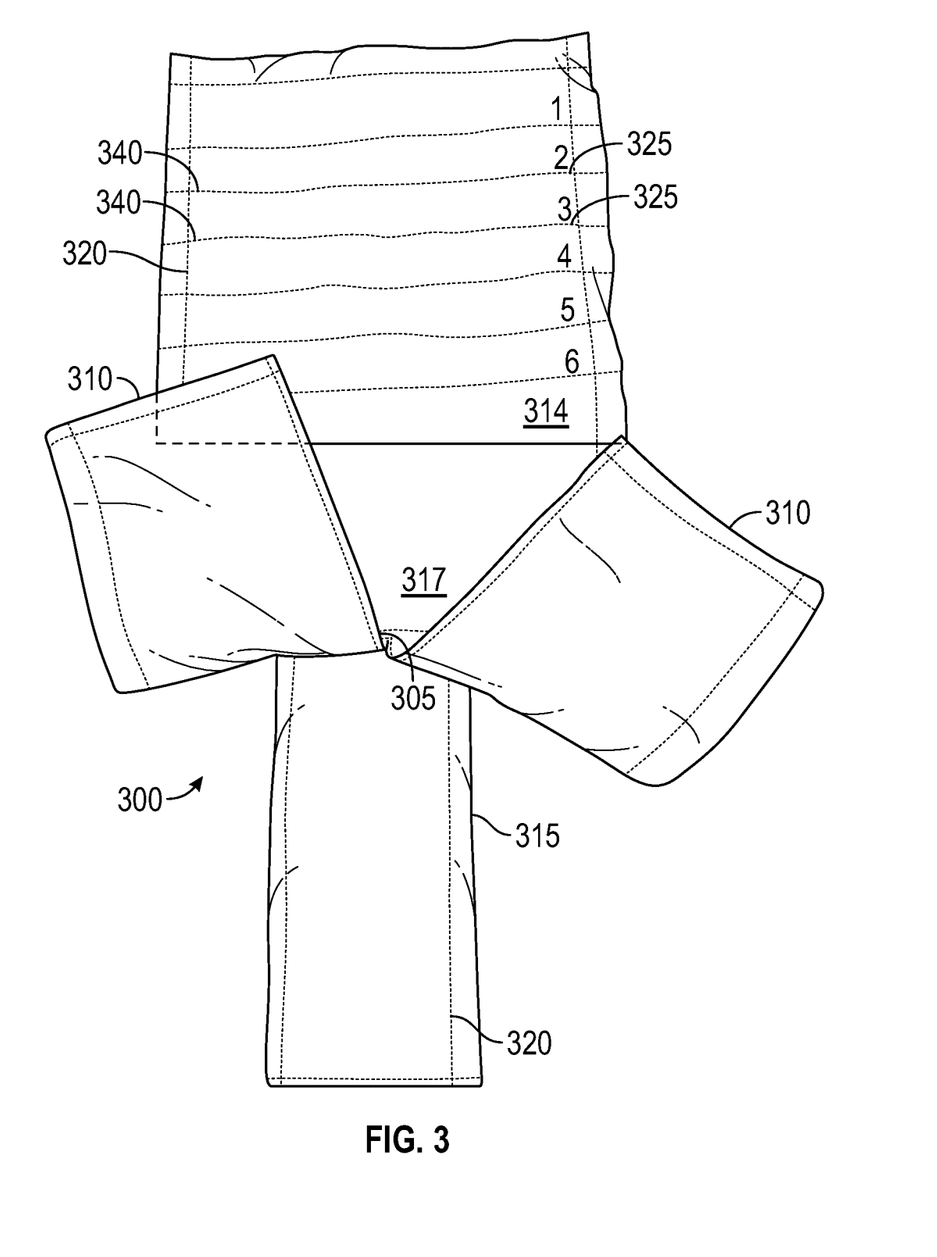
FIG. 3 is a perspective of still another suitable embodiment of an absorbent article including graduated placement indicia.

FIG. 3 is a perspective of still another suitable embodiment of a disposable absorbent article 300 including graduated placement indicia 325 optionally perforated for removal of excess liner material at perforations 340 per a user's preference. Absorbent article 300 includes an upper portion 314 and a lower or bottom portion 317. The upper portion 314 may include at least one or two layers of fiber, napkin, or paper based absorbent material (one or two-ply). The lower portion 317 may include at least one, two, or three layers of fiber, napkin, or paper based absorbent material (one, two, or three-ply). The absorbent article 300 can also include at least one split, slit, or cleft 305, at least two flaps 310, at least one adjunct flap 315 overlapping the split 305, and connecting means 320, for instance sewn stitching connecting the multiple layers or napkins.

The at least two flaps 310 and the at least one adjunct flap 315 in the lower portion 317 are configured or structured to engage over and with the undergarment crotch whether the user comfortably "wears" or places his genitals or scrotum to his left, center, or right. The split 305 facilitates the anchoring of at least one flap 310 or 315 on the right or left side or center for more absorbency and a customized comfort placement that minimizes movement of the absorbent article 300 once its inserted or installed. The adjunct flap 315 allows for even more flexible placement of more absorbency within the crotch region as desired by the user. The graduated placement indicia 325 allow the user to find and remember the most appropriate placement of the absorbent article 300 for his torso size and body build. As described in more detail below with respect to FIGS. 5-7, the top portion 314 is placed over the top of the user's underwear at the same indicia marking once the user finds the most appropriate fit or placement.

Figure 4:
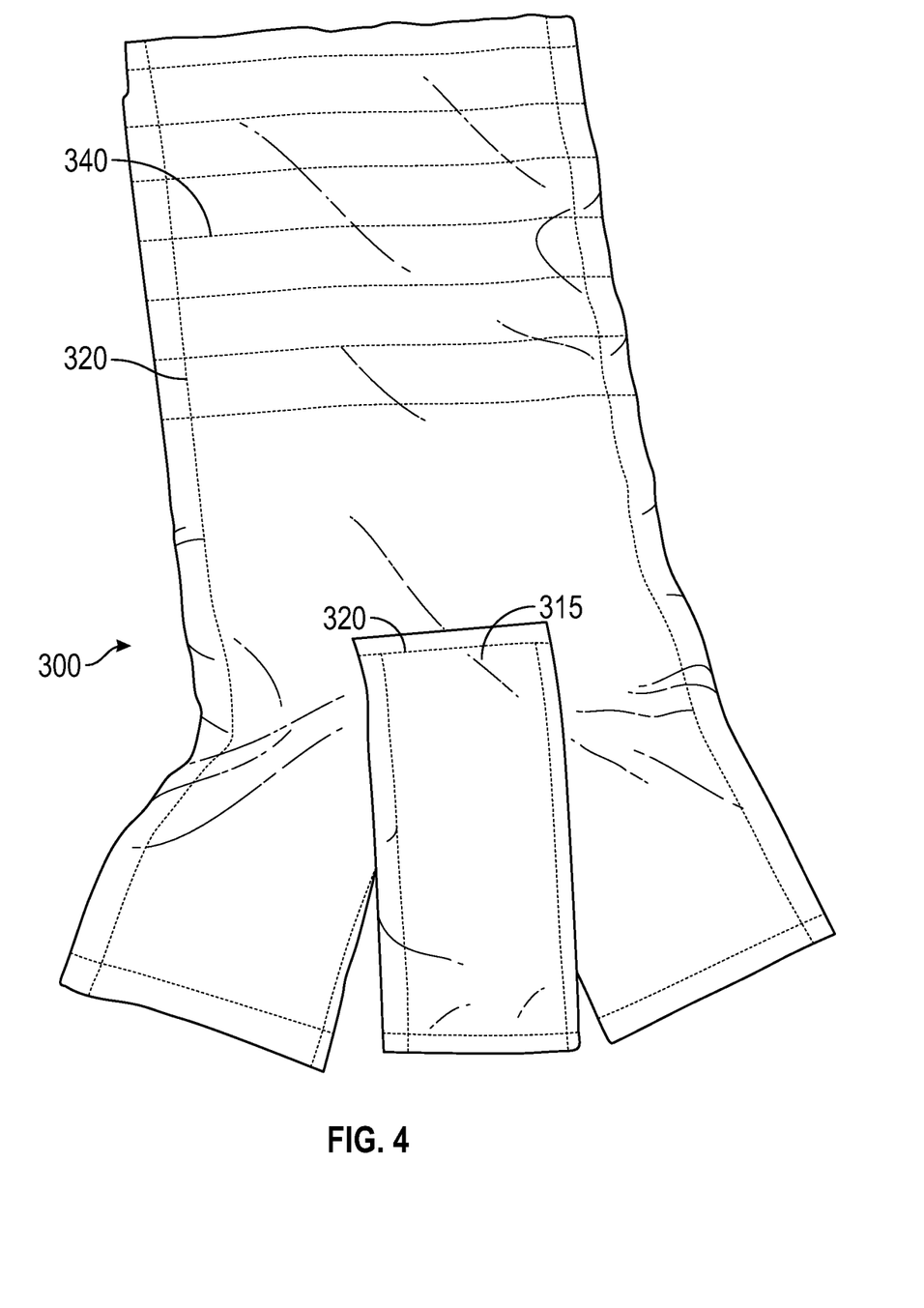
FIG. 4 is a bottom view of the absorbent article of FIG. 3.

FIG. 4 is a bottom view of the disposable absorbent article 300 of FIG. 3 that illustrates an undergarment or clothing-side view of the adjunct flap 315 in addition to the other components described in FIG. 3.

Figure 5A:
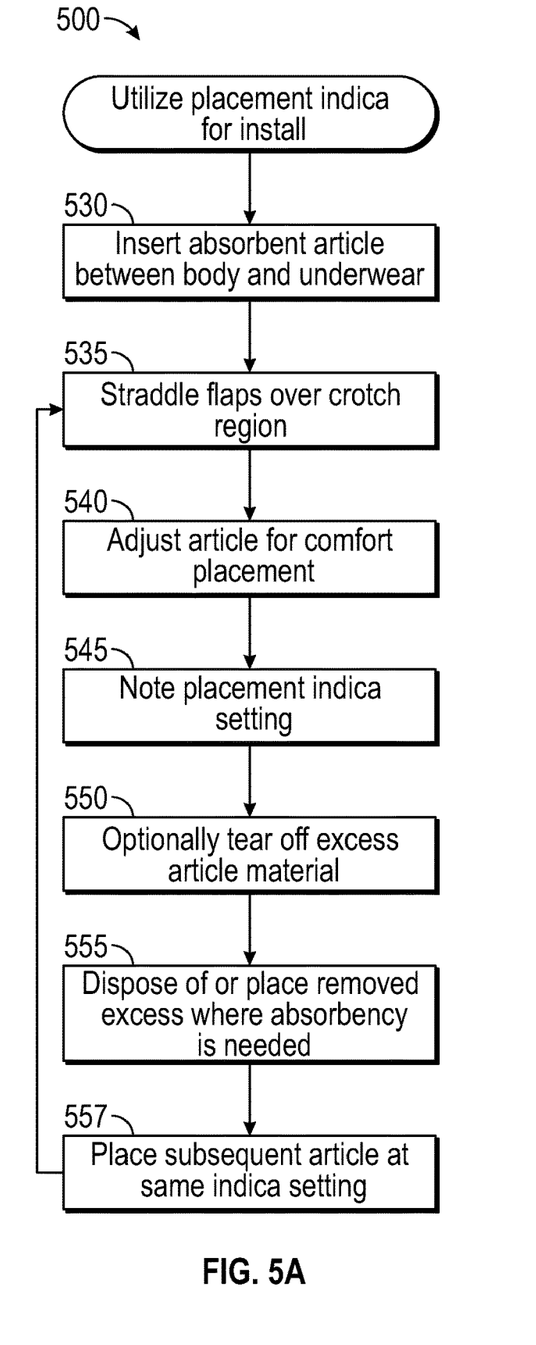
FIGS. 5A-5B are a method flow of utilizing the placement indicia of the absorbent article of FIG. 3 in conjunction a waistband of underwear to restrict movement of the absorbent article with respect to the underclothing and a perspective of an absorbent article in use engaging the crotch of the underwear.
Figure 5B:
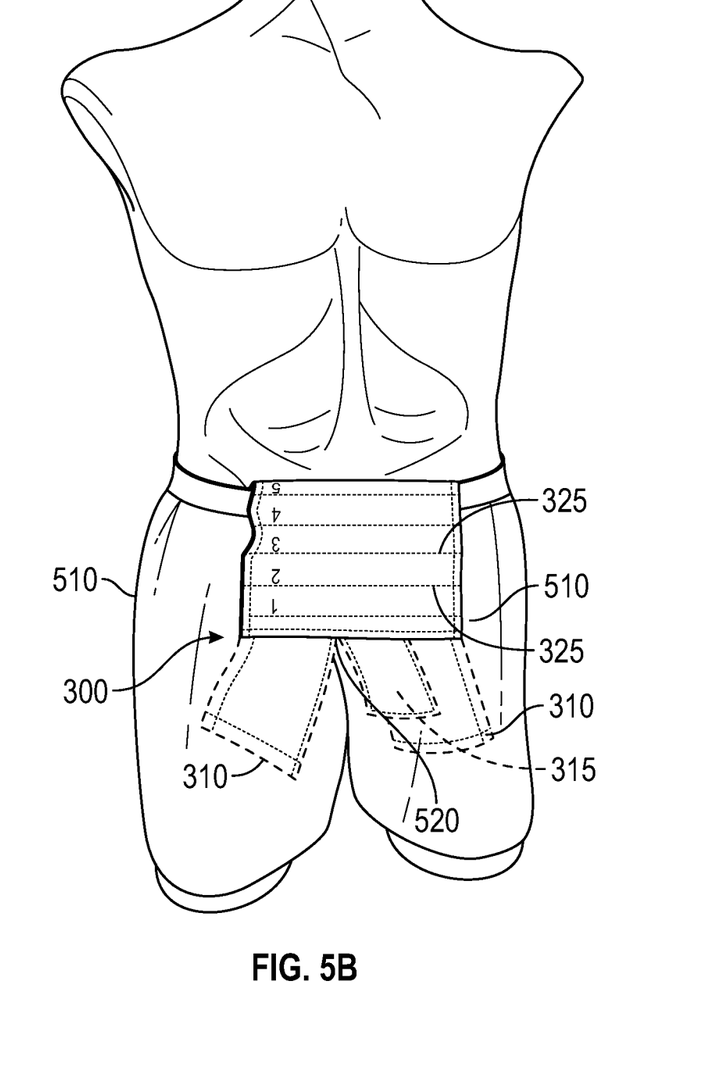

FIG. 5 is a perspective view of the absorbent article 300 in use engaging the crotch region or crotch 520 of undergarment 510 and a flow chart of the method 500 utilizing the placement indicia 325 of the absorbent article 300 of FIG. 3 in conjunction with men's undergarment or underclothing 510 as the article 300 is anchored engaging a crotch region 520 of the men's underclothing 510 via flaps 310 and adjunct flap 315. The method 500 includes: step 530 inserting the absorbent article 300 between the user's body and the undergarment 510; step 535 straddling the flaps 310, and optionally flap 315, on corresponding sides of the crotch 520; step 540 placing top portion 314 of the absorbent article 300 over the waistband of undershorts or underwear 510 at the graduated placement indicia marking 325 that comfortably fits a torso or body make up of the user. If a user finds that the fit or placement is too loose or too tight he may adjust the absorbent article 300 to next placement indicia 325 to confirm a better or correct placement; step 545 noting the chosen placement indicia setting that comfortably fits; step 550 optionally removing excess upper portion 314 article material at or near perforations 340 adjacent to placement indicia fold-over. step 555 optionally disposing of or placing removed excess material where absorbency is needed adjacent to the absorbency article 300; and step 557 optionally placing a subsequent absorbent article 300 at the previously determined placement indicia setting and returning to step 535.

Figure 6:
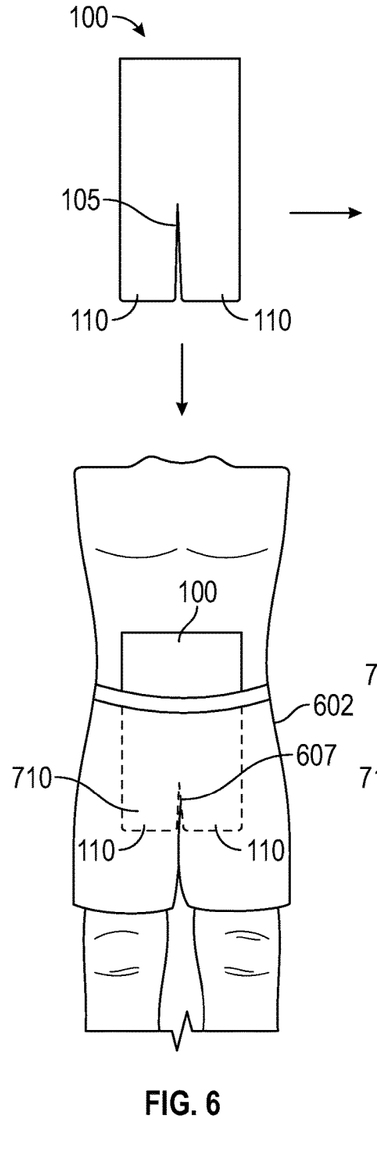
FIG. 6 is a frontal perspective of an absorbent article before and at initial placement inside the undergarment engaging the undergarment crotch.

FIG. 6 is a frontal perspective of the absorbent article 100 before and at initial placement inside the undergarment or undershorts 602 engaging the undergarment crotch region 607. The absorbent article 100 can be inserted or installed between the undershorts 602 and the user's genital region where the absorbent flaps 110 straddle the crotch region 607 of the undershorts 602 as described above with respect to process method steps 530 and 535.

Figure 7:
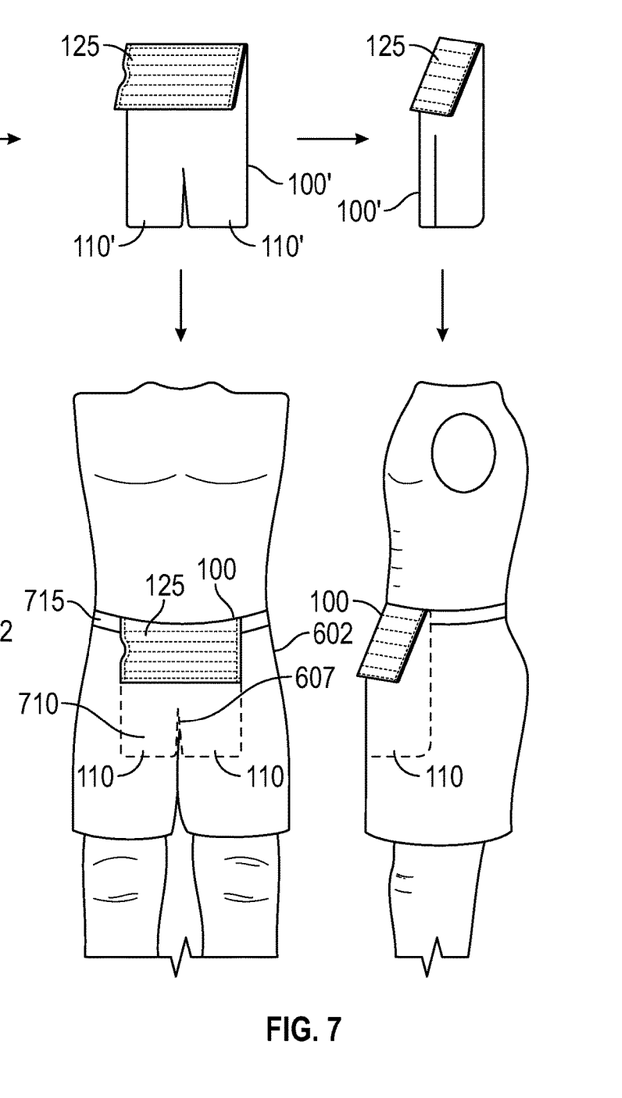
FIG. 7 is a frontal and side perspective of the absorbent article of FIG. 6 folded over and engaged with the undergarment according to the placement indicia and desired fit.

FIG. 7 is a frontal and side perspective of the absorbent article 100 of FIG. 6 folded over and engaged with the undergarment 602 according to the placement indicia 125 and desired fit. After initial insertion or install, the absorbent article 100 can be folded over the waistband of the undershorts 602 and the placement indicia 125 can be used to mark the desired fit for the user as the absorbent flaps 110 straddle the crotch 607 and extend to the upper thigh region of the users legs 710 optionally covered by the undershorts 602 as described above with respect to process method steps 540 and 545.

As described above, the method of placing the absorbent article 100 for male incontinence includes the step of folding an upper portion of the article having laterally disposed indicia 125 over a waistband 715 of underclothing 602. This placement restricts downward and upward movement of the article 100 with respect to the underclothing 602. The indicia 25 indicate a location best fitting a user. The method further includes straddling the crotch 607 of the underclothing 602 with the flaps 110 and split 105 thus, restricting a lateral and, eventually, downward movement of the absorbent article with respect to the underclothing. The split 105 may extend longitudinally toward an upper portion of the article 100 a distance between about a sixteenth of the full length of the article and about the full length of the article.

The absorbent article 100 flaps 110 are structured to: straddle the crotch 607 of the undergarment 602, restrict lateral movement of the absorbent article 100, and extend to a thigh region 710 of a user. The placement indicia 125 marked on and an upper portion of the article 100 body side sheet folds over the waistband 715 of the undergarment 602 at a placement setting desired by a user of the absorbent article, the placement setting chosen among the placement indicia 125.

When introducing elements of the present disclosure or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense. Embodiments of the present invention, for example, are described above with reference to block diagrams and/or operational step illustrations of methods, systems, and article products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention. These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole and in part. Furthermore, those of ordinary skill in the art will appreciate that the foregoing description is by way of example only, and is not intended to limit the invention so further described in such appended claims.

What is claimed is:

1. A disposable absorbent article for use with underwear and incontinence, the absorbent article comprising a single-piece pocketless construction including an upper portion integral with the absorbent article, a lower portion, a top sheet, a back sheet, and a middle sheet comprising absorbent material between the top sheet and the back sheet within the upper portion and the lower portion of the article between the top and bottom sheets, the upper portion integral with the absorbent article structured to adjustably fold over a waistband of the underwear and therein restrict movement of the absorbent article with respect to the underwear, wherein the upper portion of the single-piece pocketless construction also includes the absorbent material that increases absorbency capacity of the article inside the underwear when reducing the absorbent article fold over the waistband, the upper portion folded over the waistband outside the underwear also includes the absorbent material, and wherein the absorbent article is structured to only cover a frontal action of a body.

2. The absorbent article of claim 1, further comprising graduated indicia laterally disposed or the upper portion and body facing side of the article to allow a user to adjust to and retain a placement setting of the article and subsequent articles of the same size.

3. The absorbent article of claim 2, wherein the graduated indicia comprises numeric indicia.

4. The absorbent article of claim 2, wherein the graduated indicia comprises sequential numeric indicia and the absorbent material decreases absorbency capacity of the article within the underwear when increasing the absorbent article fold over the waistband.

5. The absorbent article of claim 1 wherein the middle sheet is made from a material selected from the group consisting of cellulose, wood pulp, rayon, cotton, polymeric fibers, and combinations thereof.

6. A method of placing an absorbent article for male incontinence comprising the steps of folding an upper portion of an article having laterally disposed graduated numeric indicia on a body side of the upper portion, over a waistband of underclothing therein restricting at least downward movement of the article with respect to the underclothing, the graduated numeric indicia indicating a location best fitting a user, the article further comprising a lower portion including at least a portion of a body side absorbent sheet, and utilizing the graduated numeric indicia to adjust the absorbent article over the waistband to include more or less absorbent material within the underclothing for proper fit, wherein the body side sheet is made from at least one liquid permeable material, wherein the upper portion folded over is integral with the article, and wherein the absorbent article is structured to only cover a frontal portion of a body.

7. The method of claim 6, further comprising straddling a crotch portion of the underclothing with at least one slit-extending longitudinally from an edge of the lower portion toward the upper portion therein restricting at least lateral movement of the absorbent article with respect to the underclothing crotch.

* * * * *